US010596019B2

(12) United States Patent
Melsheimer et al.

(10) Patent No.: US 10,596,019 B2
(45) Date of Patent: Mar. 24, 2020

(54) LOADING APPARATUS AND SYSTEM FOR EXPANDABLE INTRALUMINAL MEDICAL DEVICES

(71) Applicant: Cook Medical Technologies LLC, Bloomington, IN (US)

(72) Inventors: Jeffry S Melsheimer, Springville, IN (US); Jessica L Burke, Bloomington, IN (US); Sean D Chambers, Bloomington, IN (US); Arman Valaie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1160 days.

(21) Appl. No.: 14/947,243

(22) Filed: Nov. 20, 2015

(65) Prior Publication Data

US 2016/0074185 A1 Mar. 17, 2016
US 2017/0151075 A9 Jun. 1, 2017

Related U.S. Application Data

(63) Continuation of application No. 14/061,980, filed on Oct. 24, 2013, now Pat. No. 9,216,102, which is a
(Continued)

(51) Int. Cl.
*A61F 2/95* (2013.01)
*A61F 2/844* (2013.01)
(Continued)

(52) U.S. Cl.
CPC ............ *A61F 2/95* (2013.01); *A61F 2/844* (2013.01); *A61F 2/2436* (2013.01); *A61F 2/92* (2013.01);
(Continued)

(58) Field of Classification Search
CPC .... A61F 2/95; A61F 2/92; A61F 2/844; A61F 2002/9511; A61F 2002/9522; A61F 2002/9505; A61F 2/97
See application file for complete search history.

(56) References Cited

U.S. PATENT DOCUMENTS 2,305,261 A 12/1942 Kinley
4,014,333 A 3/1977 McIntyre
(Continued)

FOREIGN PATENT DOCUMENTS

DE 19851846 5/2000
EP 0657147 6/1995
(Continued)

OTHER PUBLICATIONS

The International Bureau of WIPO, International Preliminary Report on Patentability, dated Jun. 17, 2010, for International Application No. PCT/US2008/085510.
(Continued)

*Primary Examiner* — Kathleen S Holwerda
*Assistant Examiner* — Christina C Lauer
(74) *Attorney, Agent, or Firm* — Buchanan Van Tuinen LLC

(57) ABSTRACT

Medical device loading apparatuses, systems, methods and kits are described. A loading apparatus comprises a main body having a proximal end defining a proximal opening, a distal end defining a distal opening, and a passageway extending between the proximal and distal openings. The passageway defines a proximal chamber having a first inner diameter, a distal chamber having a second inner diameter, and a transition chamber disposed between the proximal and distal chambers. The transition chamber has an inner diameter that transitions from the larger second inner diameter to the smaller first inner diameter. The main body has a
(Continued)

separable connection that divides the main body between proximal and distal portions when disrupted. An expandable intraluminal medical device can be loaded into a delivery catheter using the loading apparatus by placing the device into the passageway such that it is in a radially-expanded configuration; pulling the device along an axial path through the loading apparatus such that the device transitions from the radially-expanded configuration to a radially-compressed configuration; and pushing the radially-compressed device along the axial path into the delivery catheter.

19 Claims, 7 Drawing Sheets

Related U.S. Application Data continuation of application No. 12/860,422, filed on Aug. 20, 2010, now Pat. No. 8,585,019.

(60) Provisional application No. 61/235,402, filed on Aug. 20, 2009.

(51) Int. Cl.
  *A61F 2/24* (2006.01)
  *A61F 2/92* (2013.01)

(52) U.S. Cl.
  CPC .......... *A61F 2002/9511* (2013.01); *A61F 2002/9522* (2013.01); *Y10T 29/53843* (2015.01)

(56) References Cited

U.S. PATENT DOCUMENTS

| | | | |
|---|---|---|---|
| 4,602,763 | A | 7/1986 | Gaylin |
| 4,635,989 | A | 1/1987 | Tremblay et al. |
| 5,486,193 | A | 1/1996 | Bourne |
| 5,725,519 | A | 3/1998 | Penner |
| 5,873,879 | A | 2/1999 | Figueroa et al. |
| 5,928,258 | A | 7/1999 | Kahn |
| 6,068,635 | A | 5/2000 | Gianotti |
| 6,090,035 | A | 7/2000 | Campbell |
| 6,096,027 | A | 8/2000 | Layne |
| 6,149,680 | A | 11/2000 | Shelso |
| 6,471,718 | B1 | 10/2002 | Staehle |
| 6,640,412 | B2 | 11/2003 | Iancea |
| 6,689,123 | B2 | 2/2004 | Pinchasik |
| 6,702,845 | B1 | 3/2004 | Cully et al. |
| 6,823,576 | B2 | 11/2004 | Austin |
| 6,859,986 | B2 | 3/2005 | Jackson |
| 6,915,560 | B2 | 7/2005 | Austin |
| 6,926,732 | B2 | 8/2005 | Derus et al. |
| 7,104,343 | B2 | 9/2006 | Roberts |
| 7,402,171 | B2 | 7/2008 | Osborne |
| 7,819,388 | B2 | 10/2010 | McCallion |
| 7,959,595 | B2 | 6/2011 | Melsheimer et al. |
| 8,262,065 | B2 | 9/2012 | Matsuyama |
| 8,359,721 | B2 | 1/2013 | Melsheimer et al. |
| 8,585,019 | B2 | 11/2013 | Melsheimer et al. |
| 2001/0001128 | A1 | 5/2001 | Holman et al. |
| 2002/0177899 | A1 | 11/2002 | Eum |
| 2003/0055492 | A1 | 3/2003 | Shaolian |
| 2003/0083730 | A1 | 5/2003 | Stinson |
| 2003/0208254 | A1 | 11/2003 | Shortt |
| 2003/0225445 | A1 | 12/2003 | Derus |
| 2004/0117012 | A1 | 6/2004 | Vincent |
| 2006/0064152 | A1 | 3/2006 | Olson |
| 2006/0167468 | A1 | 7/2006 | Gabbay |
| 2006/0183383 | A1 | 8/2006 | Asmus et al. |
| 2006/0230592 | A1 | 10/2006 | Heaney |
| 2006/0247755 | A1 | 11/2006 | Pal et al. |
| 2006/0253114 | A1 | 11/2006 | Saadat |
| 2007/0050006 | A1 | 3/2007 | Lavelle |
| 2007/0056346 | A1 | 3/2007 | Spenser |
| 2007/0061009 | A1 | 3/2007 | Spenser |
| 2007/0270931 | A1* | 11/2007 | Leanna ............... A61F 2/95 623/1.11 |
| 2007/0270932 | A1 | 11/2007 | Headley |
| 2007/0270937 | A1 | 11/2007 | Leanna |
| 2007/0282370 | A1 | 12/2007 | Brady et al. |
| 2008/0281293 | A1 | 11/2008 | Peh et al. |
| 2009/0054976 | A1 | 2/2009 | Tuval et al. |
| 2009/0143852 | A1* | 6/2009 | Chambers ............ A61F 2/0095 623/1.11 |
| 2009/0143857 | A1 | 6/2009 | Melsheimer et al. |
| 2009/0182410 | A1 | 7/2009 | Case et al. |
| 2009/0192496 | A1 | 7/2009 | Suwito et al. |
| 2009/0259287 | A1 | 10/2009 | Valaie |
| 2010/0057185 | A1 | 3/2010 | Melsheimer et al. |
| 2014/0121748 | A1 | 5/2014 | Melsheimer et al. |

FOREIGN PATENT DOCUMENTS

| | | |
|---|---|---|
| EP | 0938880 | 9/1999 |
| EP | 1362563 | 11/2003 |
| WO | 9959503 | 11/1999 |
| WO | 0040176 | 7/2000 |
| WO | 0249541 | 6/2002 |
| WO | 2007061801 | 5/2007 |
| WO | 2008091409 | 7/2008 |

OTHER PUBLICATIONS

The International Searching Authority, International Search Report and the Written Opinion, dated Mar. 26, 2009, for International Application No. PCT/US2008/085510.
The International Searching Authority, International Search Report and the Written Opinion, dated Jul. 1, 2009, for International Application No. PCT/US2009/040026.
The International Bureau of WIPO, International Preliminary Report on Patentability, dated Jun. 17, 2010, for International Application No. PCT/US2008/085495.
The International Searching Authority, International Search Report and the Written Opionion, dated Apr. 2, 2009, for International Application No. PCT/US2008/085495.
The International Searching Authority, International Search Report and the Written Opinion, dated Dec. 9, 2010, for International Application No. PCT/US2010/046181.
The International Bureau of WIPO, International Preliminary Report on Patentability, dated Mar. 1, 2012, for International Application No. PCT/US2010/046181.
USPTO, Non-Final Office Action, dated Sep. 7, 2011 for U.S. Appl. No. 12/328,157.
USPTO, Final Office Action, dated Feb. 6, 2012 for U.S. Appl. No. 12/328,157.
USPTO, Non-Final Office Action, dated Mar. 2, 2012 for U.S. Appl. No. 12/328,157.
USPTO, Final Office Action, dated Aug. 9, 2012 for U.S. Appl. No. 12/328,157.
File history of U.S. Appl. No. 12/328,157, as of Dec. 10, 2013. Filing date, Dec. 4, 2008, First Named Inventor, Jeffry S. Melsheimer. Title: Tapered Loading System for Implantable Medical Devices.
European Patent Office, PCT Office Action for application No. 10747770.5, dated Apr. 2, 2015, pp. 1-4.
USPTO, Non-Final Office Action, dated May 12, 2012 for U.S. Appl. No. 14/061,980.

* cited by examiner

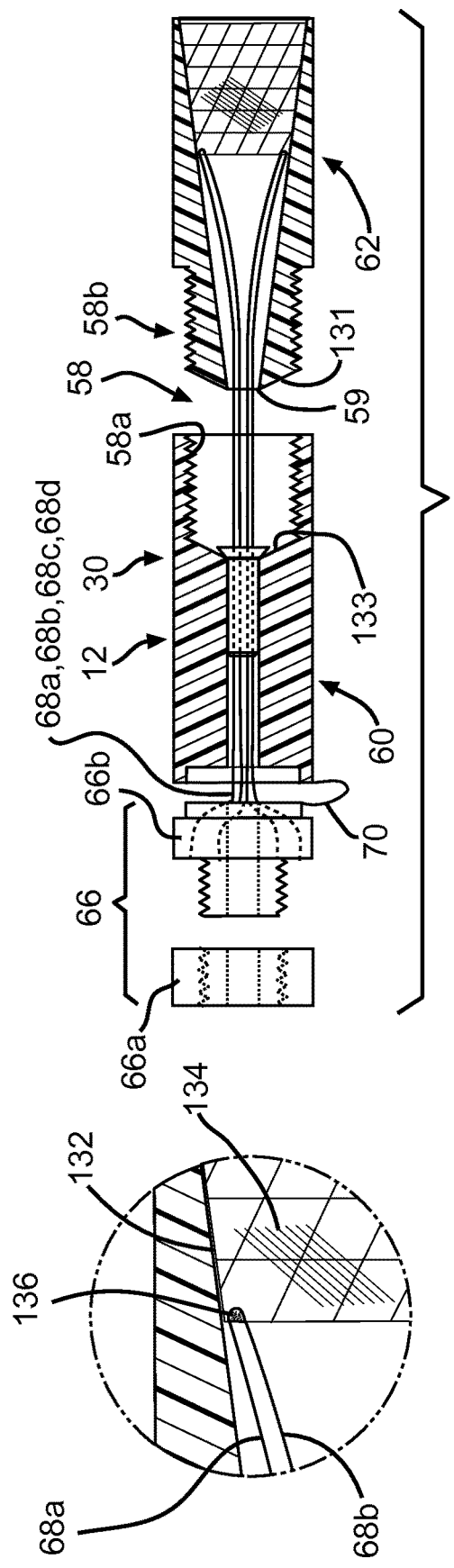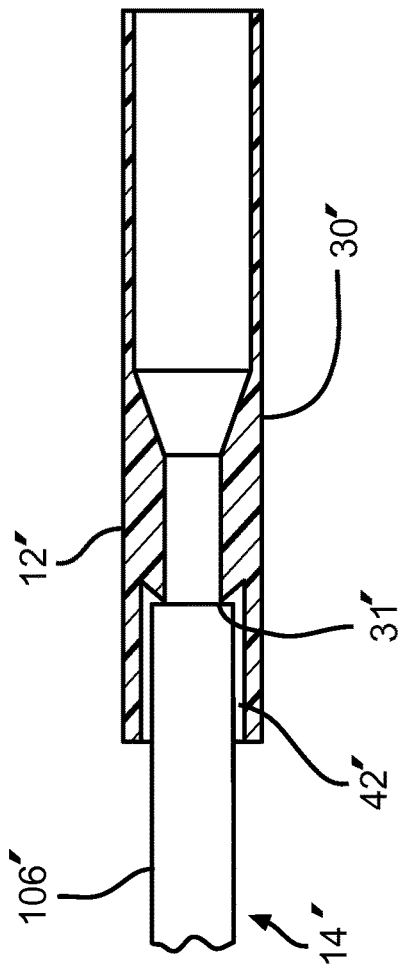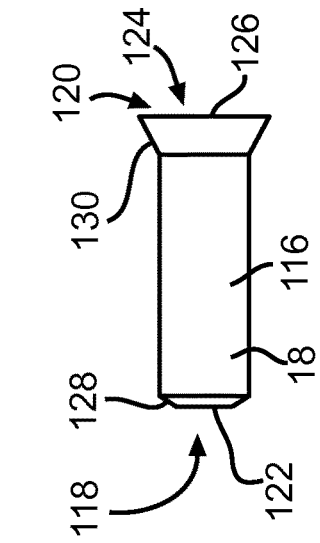

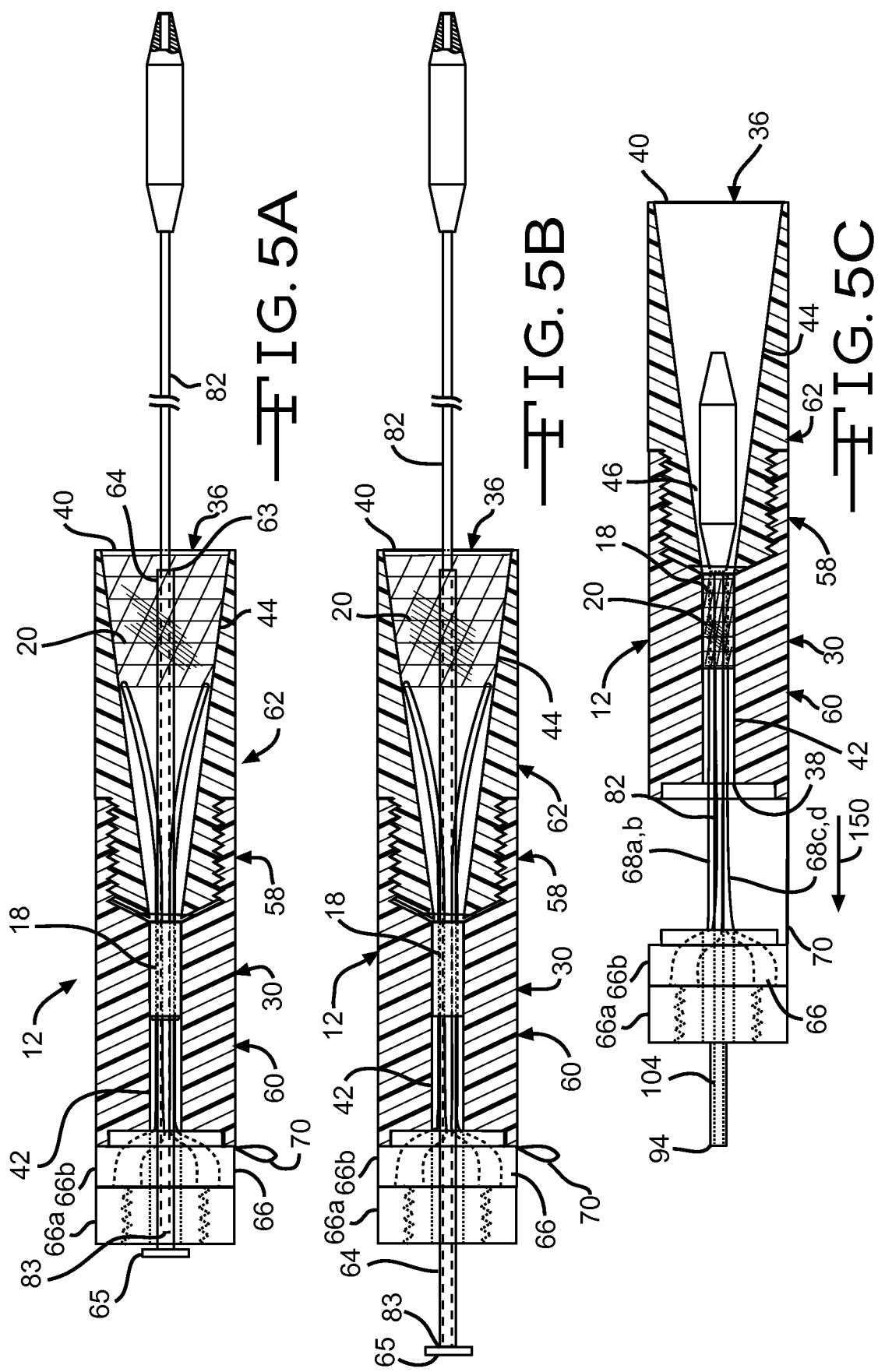

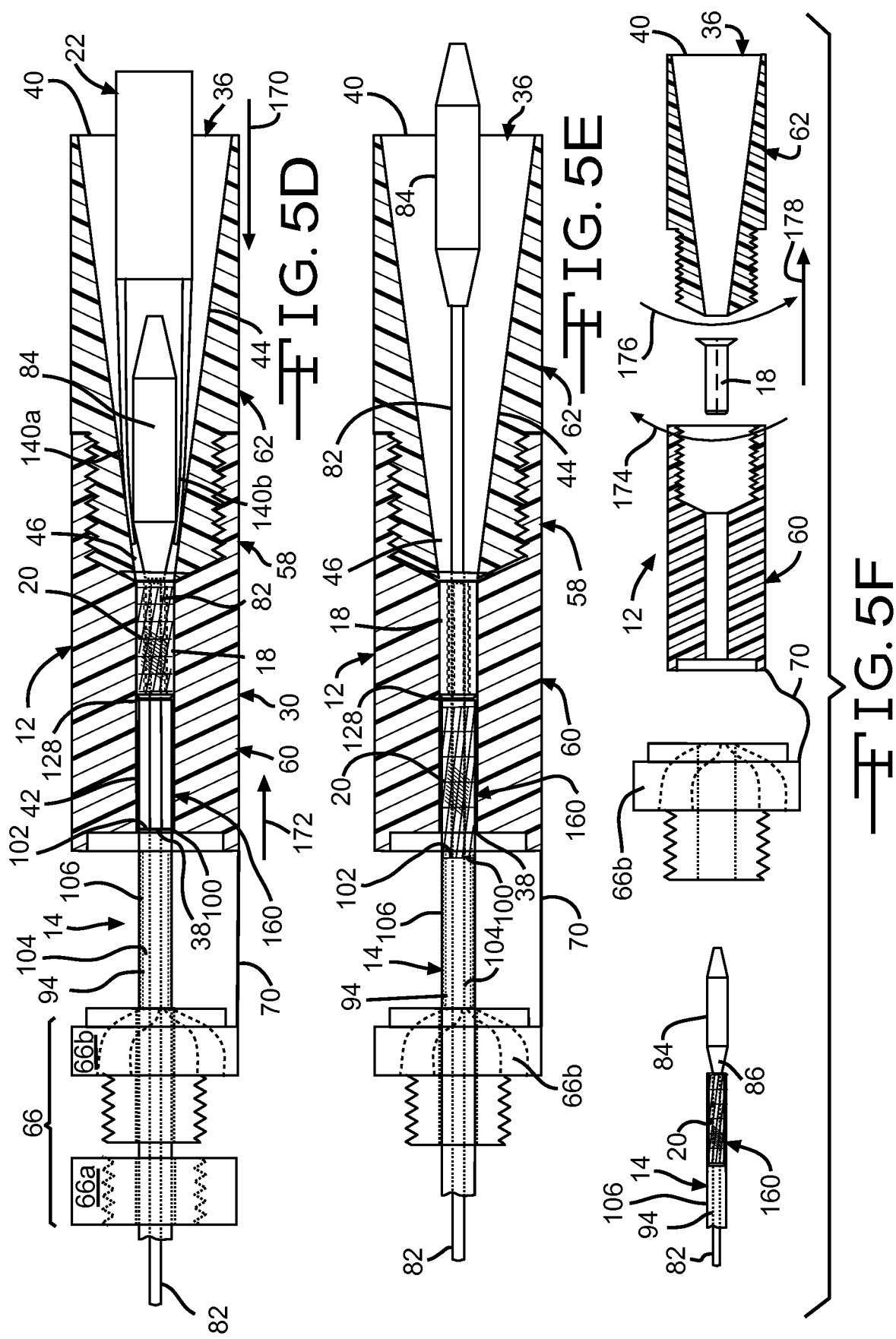

LOADING APPARATUS AND SYSTEM FOR EXPANDABLE INTRALUMINAL MEDICAL DEVICES

CROSS REFERENCE TO RELATED APPLICATION

This application is a continuation of U.S. application Ser. No. 14/061,980, filed on Oct. 24, 2013, which is a continuation of U.S. application Ser. No. 12/860,422, filed on Aug. 20, 2010, now U.S. Pat. No. 8,585,019, which claims priority to U.S. Provisional Application No. 61/235,402, filed on Aug. 20, 2009. Each of these related applications is hereby incorporated by reference into this disclosure in its entirety.

FIELD

The disclosure relates generally to the field of expandable intraluminal medical devices. More particularly, the disclosure relates to the field of expandable intraluminal medical devices that are loaded into a delivery device, such as a percutaneous delivery catheter, prior to deployment at a treatment site. Apparatuses and systems for loading expandable intraluminal medical devices, such as stents, including coronary and other stents, stent graft devices, and prosthetic valves, such as prosthetic heart valves and prosthetic venous valves, into a delivery device are described. Related kits and methods are also described.

BACKGROUND

A variety of expandable intraluminal medical devices have been developed over recent years. Stents, for example, are routinely used in several body lumens as a means for providing support to ailing vessels, such as coronary and non-coronary vessels. Stent-graft devices are frequently used to provide support from within a body vessel and/or to exclude a portion of a vessel wall from the lumen of the vessel. Prosthetic valves, including heart and venous valve devices, that include expandable support frames have also been the focus of considerable development efforts over the last several years.

Irrespective of the ultimate function of the device, expandable intraluminal medical devices are typically delivered to a point of treatment using a delivery system designed for percutaneous techniques. In a conventional procedure, a caregiver navigates the delivery system through one or more body vessels until the expandable intraluminal medical device, which is typically contained within a distal tip or portion of the delivery system, is positioned at or near the desired point of treatment. Next, the caregiver deploys the expandable intraluminal medical device from the delivery system, either by removing a constraining force for self-expandable devices or by providing an expansive force for balloon-expandable devices. Once deployment is complete, the delivery system is removed from the body vessel, leaving the expandable intraluminal medical device at the point of treatment.

During delivery, expandable intraluminal medical devices are maintained in a reduced-diameter configuration within the delivery system to ensure navigability of the delivery system through the body vessel. It is necessary, therefore, to compress the intraluminal medical device and place it within the delivery system at some time prior to use in the treatment procedure. For some devices, including some cardiac stents, this loading procedure can be conducted as part of the manufacturing process, i.e., prior to shipment to the treatment facility. For other devices, however, various concerns caution against loading the device at any time not immediately prior to delivery. For example, some tissue-based devices, such as prosthetic heart and venous valves, must be maintained in an appropriate fluid during all storage periods prior to use in a treatment procedure to ensure the integrity of the tissue component of the device. Furthermore, the effects of reduced-diameter storage of such tissue-based devices, particularly long-term storage, are not well-characterized and, as a result, are desirably avoided at this time.

A loading procedure that is conducted immediately prior to treatment is subject to several concerns not considered critical for such procedures conducted outside of the treatment theater. For example, the loading procedure must not require bulky equipment that is difficult to use and/or inappropriate for the treatment theater. The procedure must be efficient and simple, and any materials or devices used in such a procedure should be easy to handle and operate. A need exists, therefore, for a simple apparatus that facilitates loading of an expandable intraluminal medical device into a delivery device. A need for improved methods of loading expandable intraluminal medical devices into delivery devices also exists.

BRIEF SUMMARY

Apparatuses for loading expandable intraluminal medical devices into a delivery device are described. An apparatus according to one embodiment comprises a main body having a proximal end defining a proximal opening, a distal end defining a distal opening, and a passageway extending between the proximal and distal openings. The passageway defines a proximal chamber having a first inner diameter, a distal chamber having a second inner diameter, and a transition chamber disposed between the proximal and distal chambers. The second inner diameter is greater than the first inner diameter and the transition chamber has an inner diameter that transitions along an axial length of the transition chamber from the second inner diameter to the first inner diameter. The main body has a separable connection that divides the main body between proximal and distal portions when disrupted.

The separable connection can provide a separating line between the proximal and distal portions that intersects a longitudinal axis of the main body at a point where the inner diameter of the transition chamber is greater than the outer diameter of the distal tip of a delivery device intended for use with the loading apparatus.

Systems for loading and delivering expandable intraluminal medical devices are also described. A system according to one embodiment comprises a loading apparatus comprising a main body having a proximal end defining a proximal opening, a distal end defining a distal opening, and a passageway extending between the proximal and distal openings. The passageway defines a proximal chamber having a first inner diameter, a distal chamber having a second inner diameter, and a transition chamber disposed between the proximal and distal chambers. The second inner diameter is greater than the first inner diameter and the transition chamber has an inner diameter that transitions along an axial length of the transition chamber from the second inner diameter to the first inner diameter. The main body has a separable connection that divides the main body between proximal and distal portions when disrupted. The system also includes a delivery catheter comprising an outer tubular member defining a sheath lumen, a dilator body disposed within the sheath lumen and defining a dilator lumen, and a distal tip member comprising an elongate cannula and a distal tip. The elongate cannula is adapted to be slideably disposed within the dilator lumen and the distal tip member defines an outer diameter that is smaller than at least the second inner diameter of the main body of the loading apparatus.

A inner sleeve can be included to provide a mechanical lead-in to the proximal chamber of loading apparatus. The inner sleeve prevents engagement between the expandable intraluminal medical device and the leading edge of the outer tubular member of the delivery catheter during a loading procedure. Alternatively, a circumferential edge that provides a mechanical lead-in to the proximal chamber can be formed on an inner surface of the main body of the loading apparatus.

Kits useful in the loading of an expandable intraluminal medical device into a delivery device are also described. A kit according to one embodiment comprises a loading apparatus according to an embodiment, an expandable intraluminal medical device, and a delivery catheter.

Methods of loading expandable intraluminal medical devices into delivery devices are also described. Exemplary methods include one step of pulling an expandable intraluminal medical device along an axis so that it transitions from a radially-expanded configuration to a radially-compressed configuration, and another step of pushing the radially-compressed expandable intraluminal medical device along an axis and into a delivery device.

Additional understanding of the claimed invention can be obtained with review of the following detailed description and the appended drawings, which illustrate the described exemplary embodiments.

BRIEF DESCRIPTION OF THE DRAWINGS

FIG. 1A is a magnified view of the area indicated in FIG. 1.

FIG. 2 is a sectional view of the loading apparatus of the loading system illustrated in FIG. 1.

FIG. 3 is a perspective view of the inner sleeve of the loading system illustrated in FIG. 1.

FIG. 4 is a sectional view of a loading apparatus according to an alternate embodiment.

FIGS. 5A through 5F illustrate use of the loading system of the first embodiment.

FIG. 5A is a sectional view of an expandable intraluminal medical device, a loading apparatus, and a delivery catheter during an initial step of loading the medical device into the delivery catheter.

FIG. 5B is a sectional view of an expandable intraluminal medical device, a loading apparatus, and a delivery catheter during another step of loading the medical device into the delivery catheter.

FIG. 5C is a sectional view of an expandable intraluminal medical device, a loading apparatus, and a delivery catheter during another step of loading the medical device into the delivery catheter.

FIG. 5D is a sectional view of an expandable intraluminal medical device, a loading apparatus, and a delivery catheter during another step of loading the medical device into the delivery catheter.

FIG. 5E is a sectional view of an expandable intraluminal medical device, a loading apparatus, and a delivery catheter during another step of loading the medical device into the delivery catheter.

FIG. 5F is a sectional view of an expandable intraluminal medical device, a loading apparatus, and a delivery catheter during another step of loading the medical device into the delivery catheter.

DETAILED DESCRIPTION

The following detailed description and the appended drawings describe and illustrate various exemplary embodiments. The description and drawings serve to enable one skilled in the art to make and use the invention; they are not intended to limit the scope of the invention or the protection sought in any manner.

As used herein, the term "system" refers to a collection of interoperable components, one of which is a loading apparatus in accordance with an embodiment.

As used herein, the term "loading apparatus" refers to an apparatus useful in the loading of an expandable intraluminal medical device into a medical device delivery catheter or other apparatus into which such loading is desired, such as storage vessels, research equipment, sterilization containers, and other suitable apparatuses adapted to contain an expandable intraluminal medical device in a compressed or reduced-diameter configuration.

Figure 1:
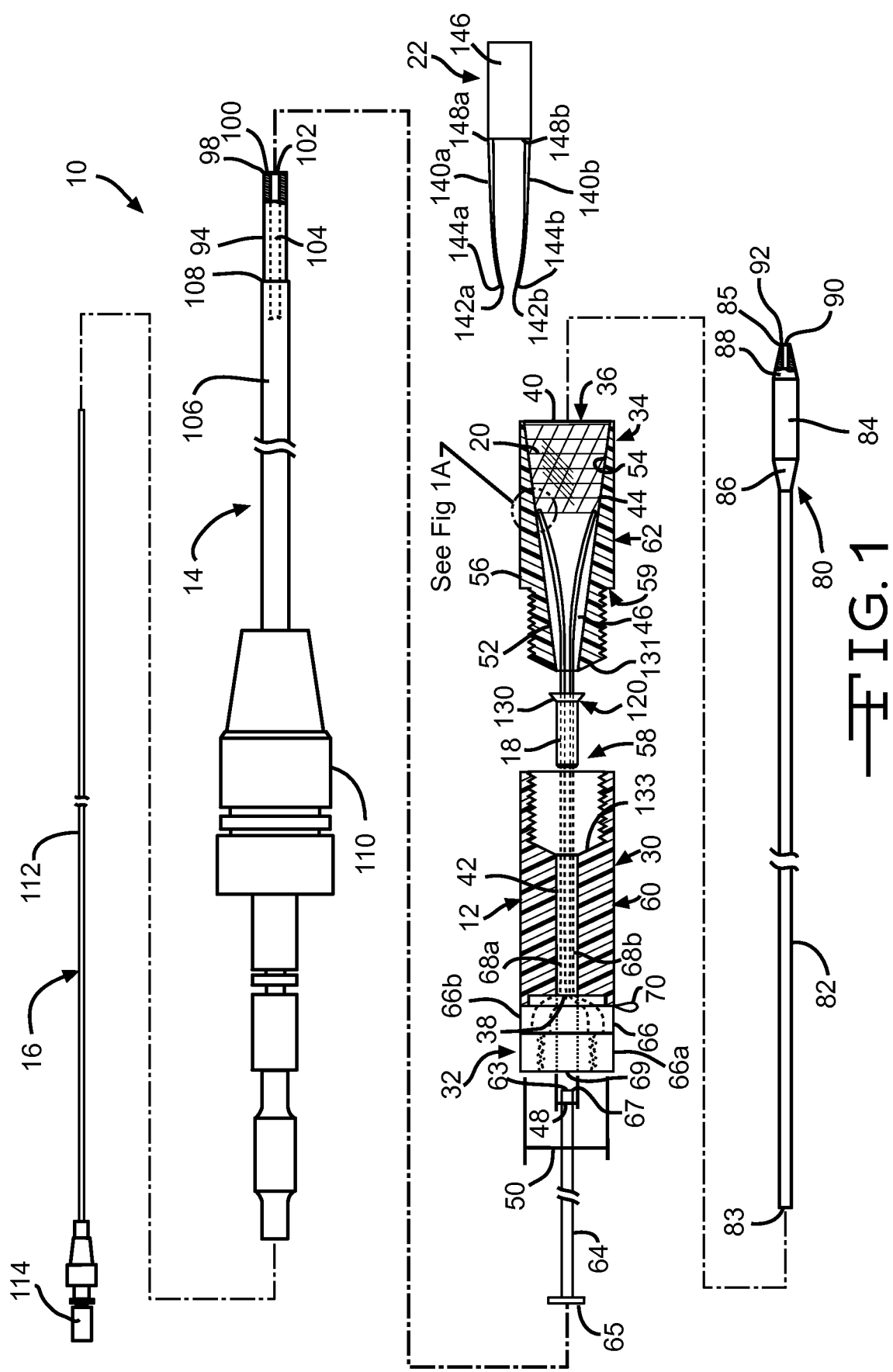
FIG. 1 is an exploded view of a loading system according to a first embodiment.

FIG. 1 is an exploded view of a system 10 for loading an expandable intraluminal medical device into a delivery catheter. The system 10 includes loading apparatus 12, delivery catheter 14, stiffening mandrel 16, inner sleeve 18, expandable intraluminal medical device 20, pusher 22, and tip member 80. As described below, some of these components are considered optional. As will be described in greater detail below, a user can load the expandable intraluminal medical device 20 into the delivery catheter 14 by advancing a distal portion of the delivery catheter 14 into a proximal portion of the loading apparatus 12, pulling the expandable intraluminal medical device 20 proximally to position it within the proximal portion of the loading apparatus 12, pushing the expandable intraluminal medical device 20 proximally to position it within the distal end of the delivery catheter 14, and removing the delivery catheter 14 from the loading apparatus 12. During the loading process, the expandable intraluminal medical device 20 transitions from an expanded configuration to a compressed configuration.

The loading apparatus 12 has a main body 30 with proximal 32 and distal 34 ends and a passageway 36 that extends between the ends 32, 34. The proximal end 32 defines a proximal opening 38 that provides access to the passageway 36. Similarly, the distal end 34 defines a distal opening 40 that provides access to the passageway 36.

The passageway 36 includes a proximal chamber 42, a distal chamber 44, and a transition chamber 46. The proximal chamber 42 has a first inner diameter 48. The distal chamber 44 has a maximum second inner diameter 50 that is larger than the first inner diameter 48. The transition chamber 46 has a transition inner diameter 52 that varies over the length of the transition chamber 46 from the second inner diameter 50 to the first inner diameter 48. As will be described more fully below, this gradually reducing transition inner diameter 52 of the transition chamber 46 provides an interior surface that compresses the expandable intraluminal medical device 20 as it is moved along a lengthwise axis of the loading apparatus 12 from the distal chamber 44 and into the proximal chamber 42.

As best illustrated in FIG. 1, the distal chamber 44 and transition chamber 46 can cooperatively define an inner surface that provides the desired transition from the second inner diameter 50 to the first inner diameter 48. It is noted, though, that alternative chamber structures can be used. For example, the transition chamber 46 can be eliminated, leaving only the proximal 42 and distal 44 chambers. In this embodiment, the distal chamber 44 includes a gradually reducing inner diameter that transitions from a first, relatively large inner diameter to a second, relatively small inner diameter. The second, relatively small inner diameter is advantageously the same as the first inner diameter 48 of the proximal chamber 42. While it can be eliminated, the inclusion of an intermediate transition chamber 46 is considered advantageous at least because it provides a greater axial length over which the expandable intraluminal medical device 20 can be transitioned from its radially-expanded configuration to its radially-compressed configuration. Also alternatively, the distal chamber 44 can include a uniform, greater second inner diameter 50. In this embodiment, the length of the distal chamber 44 can have an axial length that is equal to, substantially equal to, or greater than the axial length of the expandable intraluminal medical device 20, which allows the device 20 to have a consistent degree of expansion over its axial length while disposed in the distal chamber 44.

The passageway 36 is defined by an inner surface 54 of the main body 30. The main body 30 also includes an outer surface 56. In the illustrated embodiment, the outer surface 56 has a relatively uniform outer diameter. It is expressly understood, though, that the outer surface 56 can have a diameter that varies along the length of the main body 30, such as a diameter that substantially mimics the inner diameter as it varies along the length of the main body 30 as described above.

The main body 30 includes separable connection 58 that joins proximal 60 and distal 62 portions of the main body 30. FIG. 2 illustrates the loading apparatus 12 following separation of the proximal 60 and distal 62 portions by operation of the separable connection 58. The inner sleeve, which is held captive between the proximal 60 and distal 62 portions of the main body 30, is not depicted in FIG. 2 to better illustrate the structural arrangement of the proximal 60 and distal 62 portions. In the illustrated embodiment, the separable connection 58 comprises mating threads 58a, 58b disposed on the proximal 60 and distal 62 portions of the main body, respectively. In the illustrated embodiment, an outwardly-facing thread 58b is disposed on the distal portion 62 and an inwardly-facing thread 58a is disposed on the proximal portion 60.

While a threaded connection is illustrated for the separable connection 58, it is expressly understood that any suitable separable connection can be used for joining the proximal 60 and distal 62 portions of the main body 30. A skilled artisan will be able to select an appropriate separable connection for a loading apparatus according to a particular embodiment based on various considerations, including the material(s) used for the main body 30, the intended user of the loading apparatus 12, and the desired ease with which the separable connection 58 should be able to be operated to achieve separation of the proximal 60 and distal 62 portions. Other examples of suitable separable connections include magnetic connections, mechanical connections, such as twist and lock-type connections, clamp connections, and the like.

No matter the form and structure of the separable connection, it is considered advantageous that the separable connection 58 provide a separating line 59 between the proximal 60 and distal 62 portions that lies in a plane that is perpendicular, or substantially perpendicular, to a lengthwise axis of the main body 30. Furthermore, positioning the separating line 59 provided by the separable connection 58 along the length of the transition chamber 46 is considered desirable at least because the transition diameter 52 ensures that the distal portion 62 of the main body 30 can be passed over the distal tip body 84 of the tip member 80 following a loading procedure, as will be described more fully below. Thus, the inner diameter of the passageway 36 at the separating line 59 is advantageously greater than the outer diameter of the distal tip body 84 of the tip member 80. Also, as described more fully below, the first inner diameter 48 is also advantageously greater than the outer diameter of the distal tip body 84 of the distal tip member 80. As used herein, the term "separating line" refers to an interface between two components and includes the opposing surfaces of components that can be connected via a separable connection, such as the proximal 60 and distal 62 portions of the main body 30 when these portions are joined at separable connection 58.

The loading apparatus 12 can be formed of any suitable material, such as glass, plastic, and other suitable materials. A skilled artisan will be able to select an appropriate material based on various considerations, including the nature of the expandable intraluminal medical device 20 and any required sterilization processes that must be used. If the expandable intraluminal medical device 20 includes biological tissue that must be or may be sterilized, such as by gamma irradiation or other techniques, an appropriate material able to withstand these processes should be selected for the loading apparatus 12. Also, materials able to withstand prolonged exposure to storage fluids, including conventional storage fluids such as saline, are considered advantageous. For at least these reasons, glass and plastic materials are currently preferred for loading apparatuses intended to be used with such intraluminal medical devices. While glass is considered an acceptable material, it is less preferred than plastic materials because of its tendency to become more tacky following exposure to ethylene oxide during sterilization cycles. Plastic materials are considered particularly advantageous at least because of their ready availability, suitability for machining and other forming techniques, well-characterized nature, and acceptance in the medical arts.

No matter the material selected, a lubricious coating can be used to facilitate movement of the expandable intraluminal medical device 20 through the passageway 36 of the loading apparatus 12 during a loading procedure. For example, the inner surface 54 of the loading apparatus 12 can be coated with a suitable lubricious coating known in the medical device art. The inventors have determined that a coating layer of parylene-C on the inner surface 54 reduces the force needed to move an intraluminal medical device from the distal chamber 44 and into the proximal chamber 42, as compared to the force needed to accomplish the same movement in a loading apparatus 12 with an uncoated inner surface 54. In one test, a pull force of 5-10 lbf was required for an uncoated main body, while a pull force of <3 lbf was required for a parylene-C coated main body. A coating that provides different and/or additional benefits can also be applied to the inner surface 54. For example, a coating that protects the material of the main body 30 from any chemicals used in the fabrication of the intraluminal medical device 20 may be advantageous.

A guide tube 64 is disposed through the passageway 36. As described more fully below, the guide tube 64 is, before a loading procedure is initiated, disposed in or inserted in the passageway 36. The guide tube 64 advantageously has a length that allows it to extend through at least the axial length of the proximal chamber 42 and into the lumen defined by the expandable intraluminal medical device 20. To facilitate the overall loading process, a guide tube 64 with a length that is equal to, substantially equal to, or greater than an axial length of the main body 30 of the loading apparatus 12 is considered particularly advantageous.

The guide tube 64 defines a guide passageway 63 through which the cannula 82, described below, can be inserted during a loading procedure. While the inclusion and use of the guide tube 64 is optional, it is considered advantageous at least because it provides a physical barrier between the expandable intraluminal medical device 20 and the cannula 82 during a loading procedure. This barrier can protect the expandable intraluminal medical device 20 from potential damage-causing contact with the cannula 82. This can be particularly advantageous for expandable intraluminal medical devices that include a graft member, tissue section, or other component that might be susceptible to damage during contact with components like the cannula 82. Following initial insertion of the cannula 82, the guide tube 64 can be removed.

The guide tube 64 can be formed of any suitable material, including metal, glass, plastic, rubber, and other materials. The use of a flexible material is considered advantageous at least because it facilitates removal of the guide tube 64 following insertion of the elongate cannula 82 during a loading procedure. The guide tube 64 has proximal 65 and distal 67 ends. At least one of the ends 65, 67 is open to allow insertion of the cannula 82 during a loading procedure. Advantageously, one of the ends 65, 67 is closed, either by inclusion of a plug, cap, or other closure member, or by the inclusion of a closed end on the tube 64. The end 65, 67 that is closed should be opposite the end 65, 67 into which the cannula 82 will be inserted during a loading procedure. This arrangement ensures that the guide tube 64 is forced out of the loading apparatus 12 by the cannula 82 by its passage into the tube 64. In the illustrated embodiment, the proximal end 65 is closed and the distal end 67 is open, providing access to the guide passageway 63. Passage of the elongate cannula 82 through the distal end 67 and into the guide passageway 63, as described below, will force the guide tube 64 out of the loading apparatus 12 as the elongate cannula 82 contacts the closed proximal end 65 and is continually advanced in a proximal direction. This ensures that the guide tube 64 is removed from the loading apparatus 12 during the loading procedure.

A cap 66 is disposed on the main body 30 at the proximal opening 38. The cap defines an opening 69 through which the guide tube 64, if present, can extend. The cannula 82 of the distal tip member 80 and an outer tubular member 106 of the delivery catheter 14 can also be passed through the opening 69 during a loading procedure, as described below. Pull wires 68a, 68b are attached to cap 66 and to a structural feature of the expandable intraluminal medical device 20. As a result of these attachments, the cap 66 can be used to pull the expandable intraluminal medical device 20 through a portion of the passageway 36, such as from the distal chamber 44, through the transition chamber 46, and into the proximal chamber 42. A tether wire 70 is attached to the cap 66 and to the main body 30. The tether wire 70 advantageously has a length that prevents such axial movement of the expandable intraluminal medical device 20 beyond a desired stopping point, such as a location within the proximal chamber 42. Thus, the tether wire advantageously has a length that is less than the axial length of the main body. More advantageously, the tether wire has a length that is less than half the axial length of the main body.

Any suitable material can be used for the cap 66, including plastic, metal, glass, and rubber materials. Furthermore, the cap 66 can define structural features, such as a thread, shoulder, an included magnet or other structure that facilitates attachment to the proximal end 32 of the main body 30, which can define or otherwise provide suitable complimentary structure and/or features. Separate members can also be used to form a connection between the cap 66 and the main body 30, such as clamps and the like. As best illustrated in FIG. 2, cap 66 advantageously includes separable portions 66a, 66b. The separable portions 66a, 66b can be connected to each other by mating threads, as illustrated, or by any other suitable structure or components. The inclusion of separable portions 66a, 66b is considered advantageous at least because it allows the pull wires 68a, 68b, 68c, 68d to be clamped between the separable portions 66a, 66b during a loading procedure and removed from the expandable intraluminal medical device 20 following the procedure without requiring cutting of the wires. For example, the separable portions 66a, 66b can simply be disconnected from each other, or loosened relative to each other, allowing the pull wires 68a, 68b, 68c, 68d to simply be pulled through a loop or other structural feature on the expandable intraluminal medical device 20 and removed.

Any suitable material can be used for the pull wires 68a, 68b, 68c, 68d and the tether wire 70. As used herein, the term "wire" does not require any specific material or type of material and is used only to mean an elongate structure capable of being used as described herein. The term requires no specific degree of rigidity or stiffness. Examples of suitable materials include metal, plastic, and fibrous materials. Wires, strings, and sutures can be used for both the pull wires 68a, 68b, 68c, 68d and the tether wire 70. Furthermore, while four pull wires 68a, 68b, 68c, 68d are illustrated and described, and a single tether wire 70 is illustrated and described, any suitable number, configuration and arrangement can be used for each of these elements. The tether wire 70 is advantageously shorter in length than all of the pull wires 68a, 68b, 68c, 68d, thereby providing the desired mechanical stop.

As will be described more fully below, the pull wires 68a, 68b, 68c, 68d are advantageously disconnected from at least the expandable intraluminal medical device 20 after the device 20 has been moved into the proximal chamber 42. As such, a material that facilitates such disconnection is considered advantageous. A simple suture looped through a portion of a support frame of an expandable intraluminal medical device is considered particularly advantageous for this reason—sutures can be readily cut and removed using scissors or another cutting instrument.

Figure 8A:
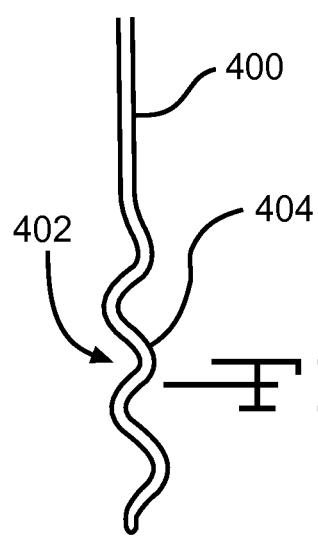
FIG. 8A is a perspective view of an alternative pull wire structure.
Figure 8C:
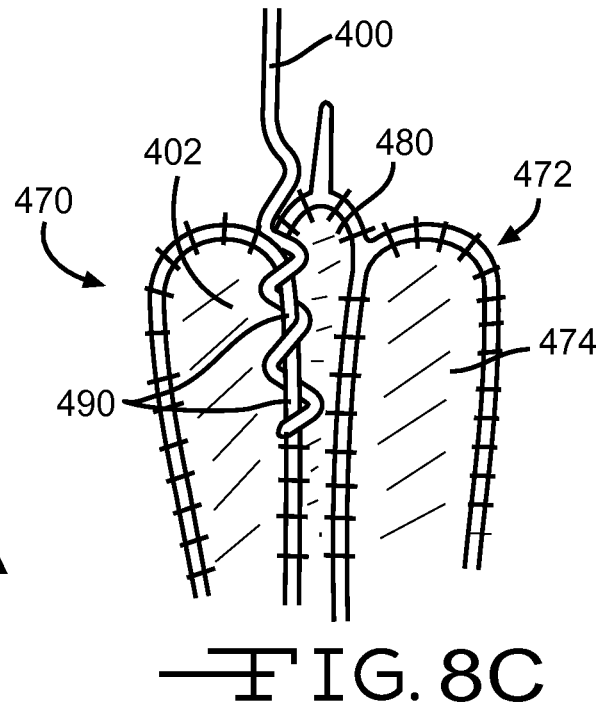
FIG. 8C is a partial perspective view of the alternative pull wire structure illustrated in FIG. 8A engaging a strut of a support frame of an expandable intraluminal medical device that includes a graft member.
Figure 8B:
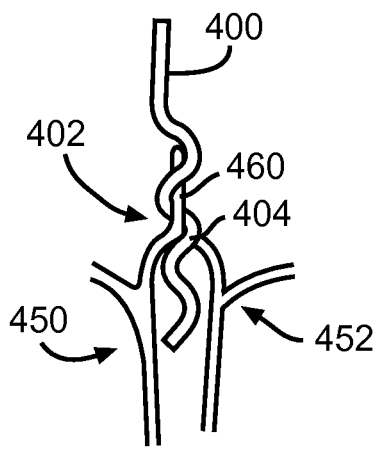
FIG. 8B is a partial perspective view of the alternative pull wire structure illustrated in FIG. 8A engaging a strut of a support frame of an expandable intraluminal medical device.
Figure 8D:
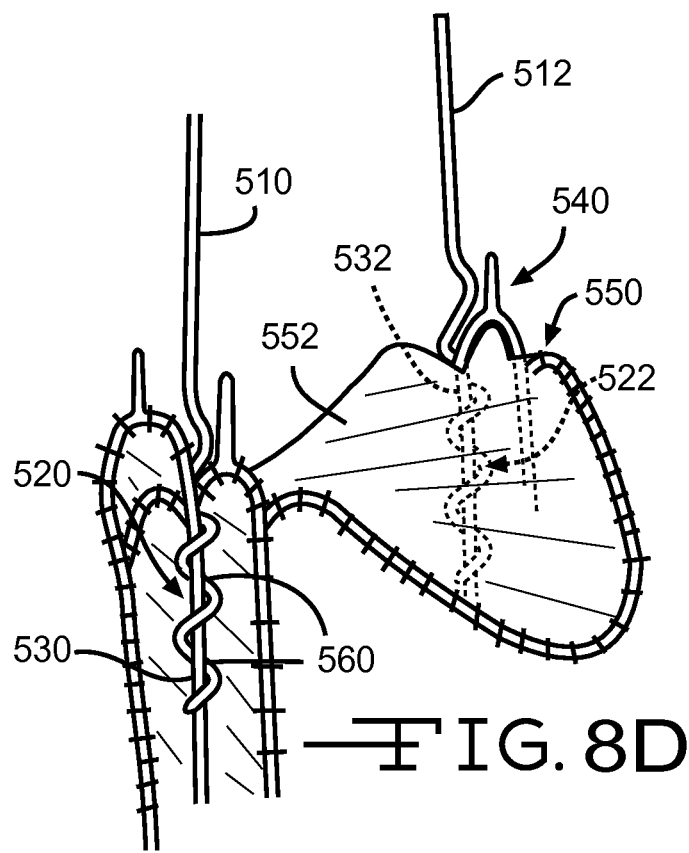
FIG. 8D is a partial perspective view of two alternative pull wires engaging struts of a support frame of an expandable intraluminal medical device that includes a graft member.

Alternatively, one or more stiff wire members that define appropriate structure for releasably engaging the expandable intraluminal medical device 20 can be used as the pull wires. For example, one or more wire members that define a helical structure at the distal end thereof can be used. The helical structure(s) can be releasably wound around a portion of the expandable intraluminal medical device, such as a strut or portion of a strut that is free of contact with an included graft or attached functional component of the device. In this embodiment, the pull wire(s) can be disconnected from the expandable intraluminal medical device following pulling of the device into the compressed configuration by rotating the pull wire(s) about a longitudinal axis while gently pulling back on the wire(s), effectively unwinding the wire(s) from around the strut or portion of a strut around which the distal end is wound. FIG. 8A illustrates a wire member 400 that defines a helical structure 402 at its distal end 404. FIG. 8B illustrates the helical structure 402 wound around a strut 460 of a support frame 452, which is part of an expandable intraluminal medical device 450. FIG. 8C illustrates the helical structure 402 would around a strut 480 of a support frame 472, which is part of an expandable intraluminal medical device 470. The expandable intraluminal medical device 470 includes a graft member 474, which can comprise a section of tissue attached to the support frame 472. In this embodiment, the helical structure 402 is wound around the strut 480 such that portions 490 of the helical structure 402 are disposed between the graft member 474 and the strut 480. FIG. 8D illustrates first 510 and second 512 wire members. The first wire member defines a first helical structure 520 and the second wire member 512 defines a second helical structure 522. Each helical structure 520, 522 is would around a strut 530, 532 of a support frame 540, which is part of an expandable intraluminal medical device 550. Similar to the embodiment illustrated in FIG. 8C, the expandable intraluminal medical device 550 includes a graft member 552 attached to the support frame 540. In this embodiment, each helical structure 520, 522 is wound around a strut 530, 532 such that portions 560 of the helical structure 520, 522 are disposed between the graft member 552 and the strut 530, 532. The expandable intraluminal medical device 550 in this embodiment is similar to the implantable valve devices described in United States Patent Application Publication No. 2009/0105813 to Chambers, et al., for an IMPLANTABLE VALVE DEVICE, the entire contents of which are incorporated into this disclosure by reference for the purpose of describing suitable expandable intraluminal medical devices for use with the loading apparatuses, systems and methods described herein.

Also, as described above, the cap 66 can include separable portions 66a, 66b. In these embodiments, each pull wire 68a, 68b, 68c, 68d can simply be looped through a structural feature on the expandable intraluminal medical device 20, such as a loop, hook, eyelet, an other suitable structure defining an opening in a support frame, or any other suitable structure, and clamped between the separable portions 66a, 66b of the cap 66. After the expandable intraluminal medical device 20 has been moved into the proximal chamber 42, the pull wires 68a, 68b, 68c, 68d can be removed simply by separating the separable portions 66a, 66b of the cap 66 from each other, or by completely disconnecting the portions 66a, 66b from each other, effectively removing the clamping force on the pull wires 68a, 68b, 68c, 68d, and pulling the pull wires 68a, 68b, 68c, 68d through their connection to the expandable intraluminal medical device 20. This structural arrangement is considered advantageous at least because it eliminates the need to cut the pull wires 68a, 68b, 68c, 68d following the step of pulling the expandable intraluminal medical device 20 into the proximal chamber 42 of the loading apparatus 12 during a loading procedure. This structural arrangement of the cap 66 is considered particularly advantageous for use with pull wires that comprise threads or other members of relatively low rigidity.

The tether wire 70 advantageously is formed of a relatively durable material that does not cut easily, such as metal, plastic, or other suitable material. The tether wire 70 is advantageously more stiff and/or more rigid than the pull wires 68a, 68b, 68c, 68d.

The delivery catheter 14 includes a tip member 80 comprising an elongate cannula 82 with a distal tip body 84 disposed on a distal end thereof. The distal tip body 84 includes a tapered proximal surface 86 and a tapered distal surface 88. The distal tip body 84 defines a distal opening 90 that provides access to a passageway 92 defined by the elongate cannula 82 and that extends between and through the proximal 83 and distal 85 ends of the cannula 82.

The delivery catheter 14 also includes an elongate main body 94 having a proximal end (not shown in the Figures) and a distal end 98. A distal surface 100 defines a distal opening 102 that provides access to a passageway 104 that extends between the proximal and distal 98 ends. The elongate cannula 82 is adapted to be slideably disposed within the passageway 104.

An outer elongate tubular member 106 provides a sheath that defines a sheath lumen 108. The elongate main body 94 is slideably disposed within the sheath lumen 108. A handle 110 or other desirable apparatus is attached to the proximal end of the tubular member 106.

Stiffening mandrel 16 has an elongate body 112 adapted to be slideably disposed through the passageway 104 defined by the main body 94 and the passageway 92 defined by the distal tip member 80. A knob 114 is disposed on a proximal end of the elongate body 112 and provides a mechanical stop that prevents further distal advancement of the mandrel 16 into the passageway 104. Inclusion of the mandrel 16 is considered optional. The inventors have determined that inclusion of the mandrel 16 is advantageous when the cannula 82 is formed of a relatively soft material with insufficient column strength, such as plastic materials, for use in loading procedures that use the loading apparatus 12, such as the methods described herein. In embodiments in which the cannula 82 is formed of a relatively rigid material that provides sufficient column strength, such as stainless steel, the inventors have determined that inclusion of the mandrel 16 is not necessary.

The various components of the delivery catheter 14 can be formed of any suitable materials, including conventional delivery system materials known in the art. For example, the distal tip member 80 is adapted to be inserted into and navigated through a body vessel into which the delivery catheter 14 is intended to deliver the expandable intraluminal medical device 20. As such, the distal tip body 84 advantageously is formed of a plastic material as is known in the art. Also, a relatively soft and/or pliable material can be used. The elongate cannula 82 can be formed of metal, plastic or other suitable material. The elongate main body 94 and elongate tubular member 106 are advantageously formed of plastic materials. The stiffening mandrel 16 advantageously comprises a solid metal member, although plastic and other materials can be used.

As best illustrated in FIG. 3, the inner sleeve 18 has a tubular body 116 with proximal 118 and distal 120 ends. The proximal end 118 defines a proximal opening 122 and the distal end 120 defines a distal opening 124. A passageway 126 extends between the proximal 122 and distal 124 openings. The proximal end 118 defines a proximal detent 128 adapted to prevent distally-directed entry of the outer elongate tubular member 106 of the delivery catheter 14 into the passageway 126 of the inner sleeve 18. Advantageously, as best illustrated in FIG. 3, the proximal detent 128 comprises an inwardly-directed circumferential taper, the outer surface of which provides the desired prevention of distally-directed entry of the outer elongate tubular member 106 into the passageway 126 and the inner surface of which slightly compresses the expandable intraluminal medical device 20 as it transitions from the passageway 126 and into the sheath lumen 108, as described below. This slight compression of the expandable intraluminal medical device 20 provides a mechanical lead-in for the device 20 so that it does not engage the leading distal edge of the outer elongate tubular member 106 of the delivery catheter 14.

The distal end 120 of the inner sleeve 18 advantageously defines a distal flange 130. Advantageously, the distal flange 130 comprises an outwardly-directed circumferential taper. As best illustrated in FIG. 1, the distal flange 130 is disposed between the proximal surface 131 of the distal portion 62 of the loading apparatus 12 and the mating distal surface 133 of the proximal portion 60 of the loading apparatus 12. This structural arrangement holds the inner sleeve 18 captive between the proximal 60 and distal 62 portions of the loading apparatus 12, preventing proximal and distal movement of the inner sleeve 18 when the proximal 60 and distal 62 portions are connected to each other via separable connection 58. This captive arrangement ensures that the inner sleeve 18 will provide the desired lead-in functionality during a loading procedure, and facilitates removal of the sleeve 18 following movement of the expandable intraluminal medical device 20 into the delivery catheter 14 (see below).

Inclusion of the inner sleeve 18 provides a separate component that has an inner diameter that is smaller than the inner diameter of the outer elongate tubular member 106 of the delivery catheter 14.

The inner sleeve 18 can be formed of any suitable material, and a skilled artisan can select an appropriate material for a system according to a particular embodiment based on various considerations, including the structure of the expandable intraluminal medical device 20 and the nature of the materials used in the device 20. Examples of suitable materials for the sleeve 18 include metal, glass, plastic and other polymeric materials. Considering the sliding movement of the expandable intraluminal medical device 20 through the inner sleeve 18 during a loading procedure, it is considered advantageous to form the inner sleeve 18 of a material that provides a relatively low coefficient of friction with regard to the expandable intraluminal medical device 20. In this regard, a stiff, relatively thin-walled tubular member formed of a polymeric material, such as polypropylene, is considered advantageous. A material that provides a relatively low coefficient of friction in relation to the material of the loading apparatus 12 is considered advantageous. Fluoropolymers are considered particularly advantageous at least because of the degree of stiffness and desirable frictional properties they provide. Fluorinatedethylenepropylene (FEP) (available from Zeus, Inc., Orangeburg, S.C.) is considered a particularly advantageous material for the inner sleeve 18. Furthermore, portions of the inner sleeve 18, or the entire sleeve 18, can be coated with a suitable lubricious coating, such as parylene-C or any other suitable coating, to facilitate movement of the expandable intraluminal medical device 20 through the sleeve 18. For example, the entire inner surface of the inner sleeve 18 can be coated, if desired.

The inner sleeve 18 can have any suitable size and configuration, and a skilled artisan will be able to select suitable parameters based on various considerations, including the size and configuration of the loading apparatus 12 of the loading apparatus, the size and configuration of the expandable intraluminal medical device 20, and the size and configuration of the delivery catheter 14. The inventors have determined that an inner sleeve 18 that has an inner diameter that is one French size (about 0.013") smaller than the inner diameter of the outer elongate tubular member 106 is suitable. This relative dimensioning provides sufficient tolerance difference to account for dimensional stack up and is readily manufacturable. Thus, the size and configuration of the loading apparatus 12 and inner sleeve 18 can be determined based on the inner and outer diameters of a delivery catheter with which the loading apparatus 12 and inner sleeve 18 are intended to work. The inventors have determined that an inner sleeve comprising FEP with a wall thickness of about 0.0125" is suitable for use with a variety of loading apparatuses and expandable intraluminal medical devices.

Figure 6:
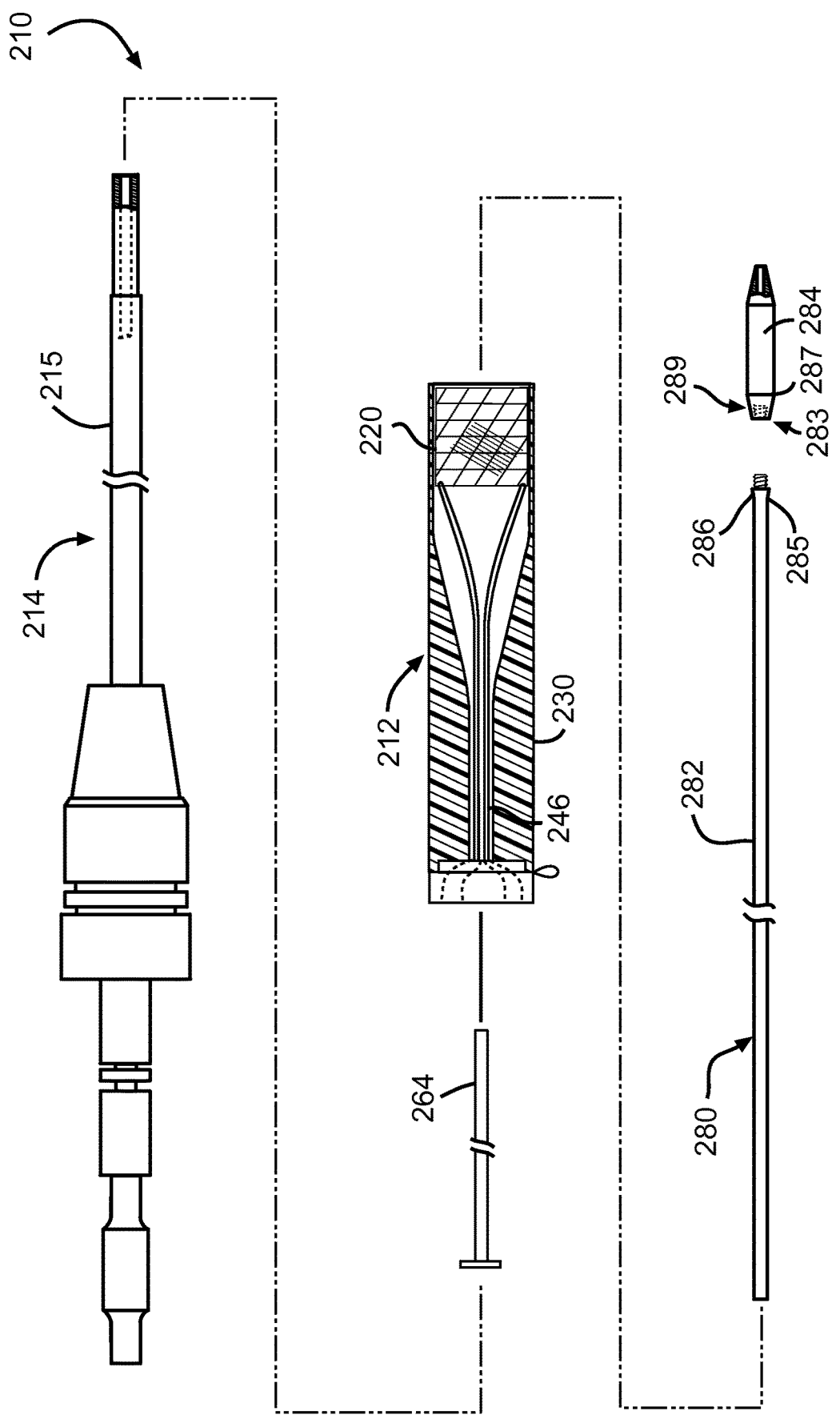
FIG. 6 is an exploded view of a loading system according to a second embodiment.

FIG. 4 illustrates a loading apparatus 12' according to an alternate embodiment in which the main body 30' defines a circumferential edge 31' that leads into an outer elongate tubular member 106' of a delivery catheter 14' that has been disposed in the proximal chamber 42'. The circumferential edge 31' defines an inner diameter that is less than an inner diameter of the outer elongate tubular member 106' and, as such, protects the distal end of the outer elongate tubular member 106' from engagement with an expandable intraluminal medical device (not illustrated in FIG. 4) during a loading procedure. Accordingly, when an expandable intraluminal medical device is pushed through the main body 30', the circumferential edge 31' provides a mechanical lead-in to the outer elongate tubular member 106' that eliminates the need for the inner sleeve used in the first embodiment described above and illustrated in FIGS. 1, 1A, 2 and 3. The structure of this alternate embodiment is considered advantageous at least because it eliminates the need for the inner sleeve, as described below. The structure of this embodiment also eliminates the need for inclusion of the separable connection used in the first embodiment because it eliminates the need for the inner sleeve and, consequently, the need to remove the sleeve from the loading apparatus following a loading procedure. The main body 30' of this embodiment, however, has a minimum inner diameter that prevents its passage over a distal tip body, such as distal tip body 84 of distal tip member 80 illustrated in FIG. 1. Thus, use of a distal tip member that includes a removable portion of the distal tip body, such as that illustrated in FIG. 6, is considered advantageous when using a loading apparatus 12' according to this embodiment.

The expandable intraluminal medical device 20 has radially-expanded and radially-compressed configurations. That is, the expandable intraluminal medical device 20 has an expanded configuration in which the device has a first, relatively large diameter and a compressed configuration in which the device has a second, relatively small diameter. A variety of expandable intraluminal medical devices are known in the art, and the expandable intraluminal medical device 20 can comprise any suitable expandable intraluminal medical device, such as a stent, a stent-graft, a prosthetic valve, an occluder, a filter, and any other type of expandable intraluminal medical device now known or later developed. Furthermore, the expandable intraluminal medical device 20 can be a self-expandable medical device or a device that requires an application of an expansion force to achieve radial expansion and the expanded configuration, such as a balloon-expandable medical device. The disclosed apparatuses, systems, kits and methods are particularly well-suited, however, for use with self-expandable intraluminal medical devices, such as expandable intraluminal medical devices that include a self-expandable support frame.

The system 10 and various components are particularly well-suited for use with expandable intraluminal medical devices for which loading the device into a selected delivery device immediately prior to a treatment procedure is recommended or otherwise considered desirable. Examples of such expandable intraluminal medical devices include stents with biologically-active coatings, stents with attached grafts, including grafts of biological origin, and tissue-based prosthetic valve devices, such as prosthetic heart valve and prosthetic venous valves that include one or more section of tissue, tissue-derived material, or other flexible material.

The inventors have determined that the system 10 and various components are particularly well-suited for use with expandable intraluminal medical devices that include a support frame 132 and an attached section of material 134, such as a section of tissue. As best illustrated in FIG. 1A, the support frame 132 advantageously defines a suitable number of connectors 136, such as loops, openings, hooks, posts, eyelets, fillets or other suitable structural features that are adapted to engage pull wires 68a, 68b as described above.

Examples of suitable expandable intraluminal medical devices for use in the systems according to this disclosure are described in United States Patent Application Publication No. 2009/0105813 for IMPLANTABLE VALVE DEVICE, the entire contents of which are hereby incorporated by reference into this disclosure.

Pusher 22 includes first 140a and second 140b pushing arms. Each arm 140a, 140b terminates in a pushing surface 142a, 142b at the proximal end 144a, 144b and is attached to a base 146 at its distal end 148a, 148b. Each of the pushing arms 140a, 140b is an elongate member having an outward bias and a semi-circular cross-sectional shape, which facilitates the advancing and loading of intraluminal medical device 20. While two pushing arms 140a, 140b are illustrated in the Figures, it is expressly understood that any suitable number of pushing arms can be used, and the exact number included in a loading system according to a particular embodiment will depend on several considerations, including the nature of the intraluminal medical device being used with the system and the size of the loading apparatus. Embodiments having between two and five pushing arms are considered advantageous at least because the inclusion of multiple arms can distribute a pushing force applied by the arms across multiple points on the intraluminal medical device 20. Nevertheless, an embodiment with a single pushing arm is considered acceptable at least because the column strength achieved in the intraluminal medical device 20 once it is placed in the radially-compressed configuration in the loading apparatus 12 is expected to be sufficient to avoid any uneven pushing placed on the device as a result of the use of only a single pushing arm. It is also noted that while the pushing arms 140a, 140b are shown in a substantially opposing arrangement, any suitable arrangement can be used. Pushing arms arranged equidistant from each other relative to a central axis of the pusher 22 are considered advantageous at least because such an arrangement results in an even application of a pushing force onto the expandable intraluminal medical device 20 during advancement through the passageway 36 of the loading apparatus 12.

The pushing arms 140a, 140b can contact and/or interact with the intraluminal medical device 20 in any suitable manner. The proximal ends 144a, 144b of the pushing arms 140a, 140b advantageously include structure that facilitates a desired contact and/or interaction for a loading system according to a particular embodiment of the invention. The illustrated pushing arms 140a, 140b include blunt proximal ends 144a, 144b that interact with a distal end of the expandable intraluminal medical device 20. Alternative structures include a channel, notch, loop, hook, or other suitable structure that accepts a barb or other portion of a support frame of the intraluminal medical device 20. The inclusion of structure that allows for a mechanical engagement between the pushing arms 140a, 140b and the expandable intraluminal medical device 20 is considered optional because the relatively high column strength achieved in the expandable intraluminal medical device 20 once it is placed in the radially-compressed configuration inside the loading apparatus 12 is expected to be great enough that the inclusion of blunt proximal ends 144a, 144b is sufficient to achieve the desired movement of the expandable intraluminal medical device 20 along the lengthwise axis of the loading apparatus 12 and into the delivery catheter 14.

While not currently preferred, it is noted that the pushing arms 140a, 140b can be configured and used to contact another portion of the expandable intraluminal medical device 20, such as a proximal end of the device 20 or even an intermediate portion of the device 20. Furthermore, the pushing arms 140a, 140b can be configured and/or arranged to achieve the desired advancement of the expandable intraluminal medical device 20 by application of a compressive force onto the intraluminal medical device 20 or by an application of tension to a portion of the device 20.

Examples of suitable pushers for use in the systems according to this disclosure are described in United States Patent Application Publication No. 2009/0143857 to Melsheimer, et al., for TAPERED LOADING SYSTEM FOR IMPLANTABLE MEDICAL DEVICES, the entire contents of which are hereby incorporated by reference into this disclosure.

FIGS. 5A through 5F illustrate use of a loading apparatus according to the first embodiment.

In an initial step of a loading method, illustrated in FIG. 5A, the proximal 60 and distal 62 portions of the main body 30 of the loading apparatus 12 are connected at separable connection 58. The guide tube 64 is positioned in the passageway 36. The proximal end 83 of elongate cannula 82 has been inserted into the distal opening 40 of the loading apparatus 12 and into the guide passageway 63 of the guide tube 64. distal flange 130 of inner sleeve 18 is held captive between the proximal 60 and distal 62 portions of the main body 30, which are connected to each other via separable connection 58. The tubular body 116 of the inner sleeve 18 is disposed within the portion of the passageway 36 within the proximal portion 60 of the main body 30.

During this stage of loading, the expandable intraluminal medical device 20 is disposed in the distal chamber 44 of the loading apparatus 12 and is in a radially-expanded configuration.

In another step of a loading method, illustrated in FIG. 5B, the proximal end 83 of the elongate cannula 82 has been advanced proximally through the loading apparatus 12 and guide tube 64. Contact between the proximal end 83 of the elongate cannula 82 and the proximal end 65 of the guide tube 64, which is a closed end, has forced the guide tube 64 partially out of the loading apparatus 12. Once the guide tube 64 has completely exited the loading apparatus 12, the user can remove it from the loading apparatus 12 and discard it.

In another step of a loading method, illustrated in FIG. 5C, the cap 66 has been pulled in the direction represented by arrow 150. As a result, pull wires 68a, 68b, 68c, 68d have pulled the expandable intraluminal medical device 20 through the transition chamber 46 and into the inner sleeve 18 and the proximal chamber 42. The expandable intraluminal medical device 20 is in a radially-compressed configuration in this stage of loading. Tether 70 is taught, preventing further proximally-directed axial movement of the cap 66, pull wires 68a, 68b, 68c, 68d, and, as a result, the expandable intraluminal medical device 20.

In another step of a loading method, illustrated in FIG. 5D, the separable portions 66a, 66b of the cap 66 have been separated from each other and the pull wires have been removed from the loading apparatus 12 and their engagement with the expandable intraluminal medical device 20. The proximal end (not illustrated in FIG. 5D) of the cannula 82, which extends through the proximal opening 38 of the loading apparatus 12, has been passed into the distal opening 102 of the main body 94 of the delivery catheter 14. Also, following removal of the pull wires from the loading apparatus 12 and their engagement with the expandable intraluminal medical device 20, the distal end of the delivery catheter 14 has been inserted into and through the proximal opening 38 of the main body 30 and into the portion of the passageway 36 defined by the proximal portion 60 of the main body 30 of the loading apparatus 12. The elongate cannula 82 has been extended through the passageway 104 of the elongate main body 94 of the delivery catheter 14 so that the distal tip body 84 is positioned within the portion of the passageway 36 defined by the distal portion 62 of the loading apparatus 12.

Pushing arms 140a, 140b of pusher 22 have been inserted into the distal opening 40 of the loading apparatus 12 to engage the expandable intraluminal medical device 20. The outer elongate tubular member 106 of the delivery catheter 14 has been advanced distally to engage the proximal detent 128 of the inner sleeve 18. Main body 94 of delivery catheter 14 has been retracted from the distal end of the outer elongate tubular member 106, creating a device chamber 160 between the distal surface 100 of the main body 94 and the distal end of the outer elongate tubular member 106. An inner surface of the outer elongate tubular member 106 defines the outer surface of the device chamber 160. The elongate cannula 82 passes through the device chamber 160 and into the distal opening 102 of the main body 94.

To load the expandable intraluminal medical device 20 into the device chamber 160, a user can apply proximally-directed force to pushing arms 140a, 140b, in the direction represented by arrow 170 while holding the delivery catheter 14 and loading apparatus 12 stationary. A distally-directed force can be applied to the delivery catheter 14 in the direction represented by arrow 172 to resist movement of components of delivery catheter 14 as a result of the proximally-directed force 170.

Following the application of the proximally-directed force 170, the expandable intraluminal medical device 20 is disposed within the device chamber 160, as represented in FIG. 5E. At this time, the inner sleeve 18 remains surrounding the elongate cannula 82 and captive in the loading apparatus 12 between the proximal 60 and distal 62 portions of the main body 30.

To complete the loading process, the separable connection 58 is disrupted by applying opposing rotational forces, represented by arrows 174, 176 in FIG. 4F (or by other appropriate disruption based on the structure and/or properties of separable connection 58). The distal portion 62 of the loading apparatus 12 is then moved distally, represented by arrow 178, until it passes over the distal tip body 84. The distal portion 62 is then free of the delivery catheter. The inner sleeve 18, the inner diameter of which is smaller than the outer diameter of the distal tip body 84, is then cut lengthwise, or otherwise disrupted structurally along its length, to allow it to be removed from its position surrounding the elongate cannula 82. The proximal portion 60 of the loading apparatus 12, which is prevented from being passed over the distal tip body 84 before the inner sleeve 18 is removed, is then moved distally, represented by arrow 178, until it passes over the distal tip body 84 and is then free of the delivery catheter. At this point, the entire loading apparatus 12 is free of the delivery catheter 14. The cap 66, which was previously captive and surrounding outer elongate tubular member 106 of the delivery catheter 14, can also be removed at this point.

To complete the loading process, the distal tip body 84 is positioned such that the tapered proximal surface 86 or other portion of the distal tip body 84 engages the distal end of the outer elongate tubular member 106 of the delivery catheter 14. This can be accomplished either by moving the elongate cannula 82 in a proximal direction while holding the delivery catheter 14 steady, or by moving the outer elongate tubular member 106 and main body 94, and the expandable intraluminal medical device, in a distal direction while holding the elongate cannula 82 steady. When accomplishing this positioning using the later approach, care should be exercised to ensure that that loaded expandable intraluminal medical device 20 is not moved out of its position in the device chamber 160.

FIG. 6 is an exploded view of a system 210 for loading an expandable intraluminal medical device into a delivery catheter according to an another embodiment. The system 210 is similar to the system 10 illustrated in other figures and described above, except as detailed below. Thus, the system 210 includes loading apparatus 212, delivery catheter 214, expandable intraluminal medical device 220, guide tube 264, and distal tip member 280. As with the first embodiment described above, a user can load the expandable intraluminal medical device 220 into the delivery catheter 214 by advancing a distal portion of the delivery catheter 214 into a proximal portion of the loading apparatus 212; pulling the radially-expanded expandable intraluminal medical device 220 proximally along a lengthwise axis of the loading apparatus 212 to position it within the proximal, or narrow, chamber of the loading apparatus 212, effectively transitioning the expandable intraluminal medical device 220 from a radially-expanded configuration to a radially-compressed configuration; pushing the radially-compressed expandable intraluminal medical device 220 proximally along the lengthwise axis of the loading apparatus 212 to move the expandable intraluminal medical device 220 from the proximal chamber of the loading apparatus 212 into the distal portion of the delivery catheter 214; and removing the delivery catheter 214 from the loading apparatus 212. During the loading process, the expandable intraluminal medical device 220 transitions from a radially-expanded configuration to a radially-compressed configuration.

In this embodiment, the distal tip member 280 includes a separable connection 283 that, when disrupted, separates the distal tip member 280 into proximal 285 and distal 287 portions. The proximal portion 285 includes the elongate cannula 282 and a portion of the distal tip body 284. The distal portion 287 includes the remaining portion of the distal tip body 284. The separable connection 283 is located on a lengthwise axis of the distal tip body 284 to place the separating line 289 formed by the separable connection 283 on the tapered proximal surface 286, or otherwise proximal to the maximum outer diameter of the distal tip body 284. Positioning the separable connection 283 in this manner eliminates the need for the separable connection in the main body 230 of the loading apparatus 212 (as included in the embodiment illustrated in FIG. 1). When the separable connection 283 is disrupted, the distal tip body 284 can be removed temporarily. The outer diameter of the remaining portion of the elongate cannula 282, and any remaining portion of the distal tip body 284, is small enough to allow the entire loading apparatus 212 to be passed over it with distal movement following a loading procedure. Furthermore, as illustrated in FIG. 6, positioning the separable connection 283 such that the separating line is within the axial length of the tapered proximal surface provides an outwardly-directed flare that can be used to pull the expandable intraluminal medical device 220 into the transition chamber 246 during a loading procedure. As such, the inclusion of a pusher, such as the pusher 22 of the first embodiment, is considered optional in this embodiment.

The inclusion of the separable connection 283 in the distal tip body 284 is also considered advantageous because it eliminates the need for inclusion of a separate inner sleeve that guides the expandable intraluminal medical device 220 into the delivery catheter 214. In this embodiment, because a portion of the distal tip body 284 can be removed, the inner diameter of the loading apparatus 212 can be made smaller than the inner diameter of the outer elongate tubular member 215 of the delivery catheter 214 because there is no need to accommodate the larger outer diameter of the portion of the distal tip body 284 that can be removed from the distal tip member 280 (i.e., there is no need to pass the distal tip body 284 through the entire loading apparatus 212; thus, an inner diameter of a portion of the loading apparatus 212 can be made smaller than the inner diameter of the outer elongate tubular member 215).

It is noted that an inner sleeve, such as inner sleeve 18 illustrated in FIG. 3, can be used, though, with this embodiment if desired. If a sleeve is included, the main body 230 still need not include a separable connection because the remaining portion of the distal tip member 280, following disconnection of the portion of the distal tip body 284 via separable connection 283, can be passed through the sleeve to complete a loading procedure. If a sleeve is included, though, it is considered advantageous to use a main body that maintains the sleeve captive between proximal and distal portions thereof, as illustrated in FIG. 1. This arrangement ensures that the sleeve remains captive during use of the loading apparatus and eliminates the possibility that it would be mishandled or misplaced. In one such embodiment, the main body includes a separable connection, such as illustrated in FIG. 1. The proximal and distal portions of the main body are, however, permanently affixed to each other, such as by adhesive or other means for fixedly attaching two portions of a component to each other, following placement of the sleeve between these portions.

While a threaded connection is illustrated for the separable connection 283, it is expressly understood that any suitable separable connection can be used for joining the proximal 285 and distal 287 portions of the distal tip member 280. A skilled artisan will be able to select an appropriate separable connection based on various considerations, including the material(s) used for the distal tip member 280 and the desired ease with which the separable connection 283 should be able to be operated to achieve separation of the proximal 285 and distal 287 portions. Other examples of suitable separable connections include magnetic connections, mechanical connections, such as twist and lock-type connections, clamp connections, and the like.

As an alternative to separable connection 283, a distal tip member having a collapsible distal tip body, such as a fluid-filled and evacuable distal tip body, can be used to achieve a reduction in outer diameter of the distal tip body during a loading procedure, which would allow the distal tip body to pass through the entire loading apparatus 212 and into the delivery catheter 214 to complete the procedure.

Figure 7:
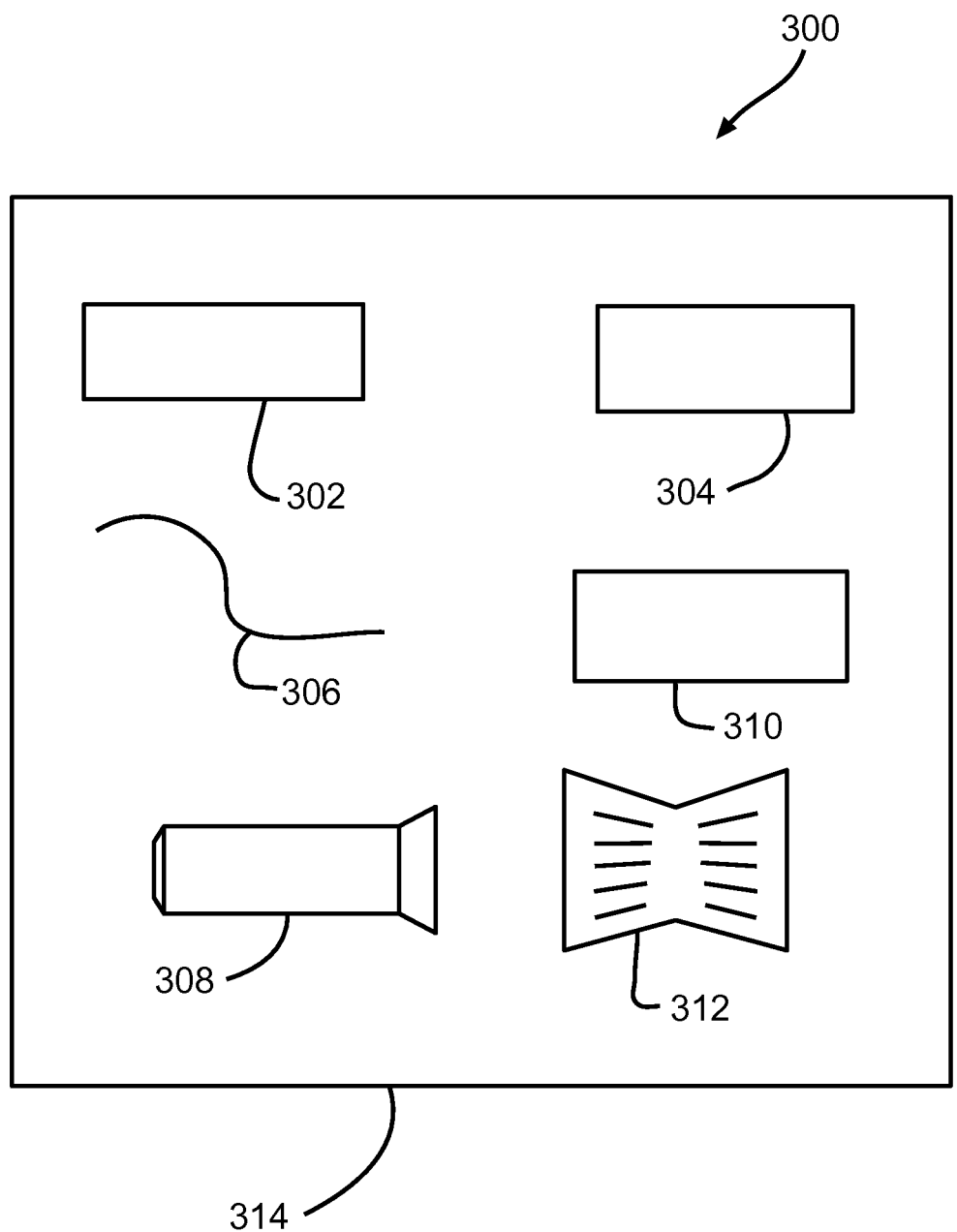
FIG. 7 is a schematic of a kit according to a third embodiment.

FIG. 7 illustrates a kit 300 useful in the preparation of an expandable intraluminal medical device for implantation in a patient. The kit 300 includes a loading apparatus 302 according to an embodiment of the invention, an expandable intraluminal medical device 304, and a delivery catheter 306. Optional components to the kit include an inner sleeve 308, a pusher 310, instructions 312 for practicing a method according to an embodiment of the invention, and a container 314 for holding the various components of the kit 300.

While the embodiments described herein relate to a loading system, the inventors expressly contemplate the use of the various components herein as a storage system as well. For example, an expandable intraluminal medical device can be placed within a loading apparatus and stored therein, such as in a distal chamber in an expanded configuration, for a period of time. In these embodiments, the loading apparatus can include caps that seal the openings at the proximal and distal ends of the loading apparatus. A storage fluid can be contained within the apparatus in these embodiments, if desired. Indeed, appropriate caps can be provided such that the loading apparatus can be placed on the delivery catheter during storage, allowing an end-user to proceed directly to loading once the delivery catheter is selected for use. Also, a loading apparatus can be stored in a storage container that includes a storage fluid and/or sealing member, such as a cap. For example, in one embodiment, an expandable intraluminal medical device can be placed within a loading apparatus and stored therein, such as in a distal chamber in an expanded configuration, for a period of time. This loading apparatus can then be placed within a storage chamber, such as a glass or plastic tube with one or more closures. Saline or another appropriate storage fluid can be placed within the storage container such that the expandable intraluminal medical device is in contact with the storage fluid, and the closure can be sealed, such as with a cap or other suitable means for closing the storage container. In this arrangement, the expandable intraluminal medical device can be stored in the loading apparatus, ready for a loading procedure, for an extended period of time.

The inventors consider it advantageous to supply the expandable intraluminal medical device to end users of the loading apparatus and/or system as disposed within the loading apparatus and ready for use in a loading procedure, such as disposed in the distal chamber of a loading apparatus in a radially-expanded configuration. Furthermore, if included, an inner sleeve is advantageously supplied to the end user in place within the loading apparatus and ready for use, such as captive between proximal and distal portions of a loading apparatus that includes a separable connection. These placements of these components ensure that the user can quickly initiate a loading procedure without concern for any pre-positioning and/or assembly steps, which might otherwise introduce variability into performance of the loading procedure. Kits according to the invention advantageously include the components arranged in this manner.

Methods of loading an expandable intraluminal medical devices into a delivery catheter are also provided. Exemplary methods include one step of pulling an expandable intraluminal medical device along an axial path and through an apparatus such that the expandable intraluminal medical device transitions from a radially-expanded configuration to a radially-compressed configuration, and another step of pushing the radially-compressed expandable intraluminal medical device along an axial path and into the distal end of the delivery catheter. The pulling and pushing steps advantageously produce movement of the expandable intraluminal medical device along a singular axial path, although movement along different and/or distinct paths can also be utilized. Furthermore, both of the pulling and pushing steps advantageously comprise translational movement (i.e., movement without rotation of the expandable intraluminal medical device). Substantially translational movement during one or both of the pulling and pushing steps is also considered suitable. Furthermore, axial movement accompanied by rotational movement of the expandable intraluminal medical device is also considered suitable for one or both of the pulling and pushing steps.

The inclusion of a pulling step is advantageous because expandable intraluminal medical devices, when in a radially-expanded configuration, are difficult to push into a delivery system. Application of a pushing force on an expandable intraluminal medical device, when in the radially-expanded configuration, is an ineffective way to move such devices along a path because the expanded device typically lacks sufficient column strength that would allow the pushing force to achieve such movement. This is particularly true for self-expandable intraluminal medical devices, such as those made of Nitinol and other flexible materials. Furthermore, the application of greater pushing force in an attempt to overcome this ineffectiveness may lead to damage to the device or an attached component, such as a graft, leaflet, or other component.

The inclusion of a pushing step, following the step of pulling the expandable intraluminal medical device into a radially-compressed configuration, is advantageous at least because there is often insufficient space in the loading apparatus, after the initial pulling step, available for components necessary to achieve the additional pulling that would be needed to accomplish the loading of the expandable intraluminal medical device into the delivery catheter. This is especially true with loading apparatuses that receive a portion of the delivery catheter, such as the outer elongate tubular member, or sheath, during the loading process, such as those described herein. For these structures, use of additional pulling force on the compressed device would require modification of the delivery catheter itself, such as inclusion of pull wires that run through at least a portion of the length of the sheath.

In contrast, by including a pushing step, the pushing force can be applied from the opposite end of the loading apparatus, i.e., the end that does not receive the delivery catheter. This enables the loading apparatuses to be used with delivery systems that do not include any special structure for pulling the radially-compressed expandable intraluminal medical device into the delivery catheter.

An exemplary method of loading an expandable intraluminal medical device into a delivery catheter includes the step of placing An expandable intraluminal medical device in a loading apparatus as described and/or claimed herein such that the device is in a radially-expanded configuration within the loading apparatus. In another step, a distal tip member or other suitable inner member is passed through the loading apparatus such that a distal tip of the distal tip member is disposed distal to the expandable intraluminal medical device. In another step, the expandable intraluminal medical device is pulled through a portion of the loading apparatus such the device is compressed and placed in a radially-compressed configuration. This pulling step can be accomplished using appropriate structure, such as the pull wires described herein. In another step, the outer elongate tubular member, or sheath, of the delivery catheter is placed into a proximal end of the loading apparatus, proximal to the compressed expandable intraluminal medical device. In another step, a pushing structure, such as those described herein, is inserted into the distal end of the loading apparatus. In another step, the pushing structure is contacted with the distal end of the expandable intraluminal medical device. In another step, a pushing force is applied to the pushing structure and, consequently, transferred onto the expandable intraluminal medical device. The pushing force is applied until the expandable intraluminal medical device is disposed within the sheath of the delivery system. Advantageously, the pushing force is applied until the expandable intraluminal medical device is disposed entirely within the distal end of the sheath of the delivery catheter, such as in a device chamber formed by the inner surface of the outer sheath and a distal end of an inner member of the catheter. In another step, the loading apparatus is removed from its position surrounding the distal tip member or other inner member. This step may include disruption of a separable connection in the loading apparatus, such as that described above, and may also include disruption and/or removal of an inner sleeve component, if used. Finally, the distal tip member is moved proximally toward and/or into the outer elongate tubular member, or sheath, of the delivery catheter until a desirable structural arrangement between these elements is achieved, such as a structure that provides a smooth transition between a distal tip body of the distal tip member and the outer surface of the outer elongate tubular member of the delivery catheter. At this point, the expandable intraluminal medical device is disposed within the delivery catheter and is ready for deployment.

While exemplary methods include one step of pulling an expandable intraluminal medical device into a radially-compressed configuration and another step of pushing the radially-compressed expandable intraluminal medical device into a medical device delivery catheter, it is noted that exclusive use of either a pushing force or a pulling force can be used to fully translate the expandable intraluminal medical device through the loading apparatus and into a delivery catheter. Exclusive use of a pushing force can be completed by simply pushing the radially-expanded medical device through the loading apparatus and into the delivery catheter. Use of the described and illustrated pusher, or another suitable structure, can be used in such methods. For exclusive use of a pulling force, the delivery catheter would need to accommodate suitable structure to achieve the desired movement. For example, pull wires, similar to those attached to the cap 66 in the embodiment illustrated in FIG. 1, could be attached to the expandable intraluminal medical device and passed through a portion or the entire length of the sheath lumen of the delivery catheter. A user could then pull the wires proximally to achieve axial movement of the expandable intraluminal medical device through the loading apparatus and placement within the device chamber of the delivery catheter. During such axial movement, the expandable intraluminal medical device would transition from a radially-expanded configuration to a radially-compressed configuration.

Example—Loading an Expandable Valve Device into a Delivery Catheter

The following example describes a method of loading an expandable valve device, which includes a self-expandable support frame and an attached bioprosthetic valve, into a suitable medical device delivery catheter. The method uses a loading apparatus as described herein, including an inner sleeve. The expandable valve device is provided in the distal chamber of the loading apparatus, in a radially-expanded configuration, prior to initiation of the loading procedure. The valve device is similar to the valve devices described in United States Patent Application Publication No. 2009/0105813 (incorporated herein, see above). The loading apparatus is provided in an outer storage container that includes a storage fluid.

1. Using a hemostat/forceps, grab the loading apparatus, such as by the guide tube if included, and remove the loading apparatus from the outer storage container, making sure that all of the storage fluid has drained out of the bottom before removing completely.

2. Insert the proximal end of the elongate cannula of the distal tip member into the distal end of the guide tube that is extended out of the loading apparatus and push until the elongate cannula is extends axially beyond both lengthwise ends of the loading apparatus. This will force the guide tube out of the proximal end of the loading apparatus. Discard the guide tube.

3. Insert the proximal end of the elongate cannula into the distal end of the main body or pusher of the delivery catheter until the proximal end of the elongate cannula exits the proximal end of the delivery catheter. At this time, the elongate cannula of the distal tip member can optionally be immobilized temporarily with respect to the main body or pusher of the delivery catheter, i.e., temporarily fix these components in position relative to each other such that relative movement between the components is not possible.

4. Pull back steadily on the cap such that the pull wires pull the valve device along the lengthwise axis of the loading apparatus, moving the valve device from the distal chamber of the loading apparatus to the proximal chamber, and transitioning the valve device from a radially-expanded configuration to a radially-compressed configuration. Stop pulling once the tether wire is taught and/or the entire valve device is inside the proximal chamber (narrow chamber) of the loading apparatus.

5. Separate the separable portions of the cap and pull the pull wires through their engagement with the valve device. Discard the pull wires. The cap is captive between the delivery catheter and the loading apparatus at this point.

6. Pull the proximal end of the main body or pusher of the delivery catheter so that the distal end of the pusher is pulled into the sheath of the delivery catheter. The distal end should be retracted into the sheath by a length that provides a device chamber of suitable axial length for receiving the valve device. Markings on the proximal end of the main body or pusher can be used to indicate a suitable positioning of the main body or pusher relative to the sheath.

7. Place the outer elongate tubular member, or sheath, of the delivery catheter into the opening defined by the proximal (narrow) end of the loading apparatus. Advance the sheath distally into the apparatus as far as the apparatus will allow such that it engages the proximal end of the inner sleeve within the loading apparatus.

8. Insert the pusher into the distal end of the loading apparatus until the pushing surface contacts the distal end of the radially-compressed valve device. Then, steadily and gently push the valve device into the delivery catheter until the valve is completely inside the device chamber defined by the sheath.

9. Disrupt the separable connection of the loading apparatus, such as by unscrewing the proximal and distal portions from each other, and remove the inner sleeve from around the cannula, such as by cutting the sleeve along its length.

10. Remove the loading apparatus components from around the elongate cannula by moving both components distally, passing over the distal tip body of the distal tip member.

11. Remove the loading apparatus cap from its position around the delivery catheter, such as by passing it completely over the distal end of the catheter and the distal tip body.

12. Advance the elongate cannula of the distal tip member proximally into the sheath until there is a smooth transition between the distal tip body and the sheath. If the distal tip member was temporarily immobilized with respect to the main body or pusher of the delivery catheter, the immobilization should be removed prior to this step, allowing relative movement between the components.

At this point, the expandable valve device is loaded in the delivery catheter and is ready for use. To prevent premature movement of the expandable valve device from the device chamber, the elongate cannula of the distal tip member can again be immobilized temporarily with respect to the main body or pusher of the delivery catheter, i.e., temporarily fix these components in position relative to each other such that relative movement between the components is not possible. If one or both of the optional immobilization steps are desired, a pin vise or other suitable apparatus can be used to temporarily lock the elongate cannula of the distal tip member to the main body or pusher of the delivery catheter.

The foregoing detailed description provides exemplary embodiments of the invention and includes the best mode for practicing the invention. The description and illustration of embodiments is intended only to provide examples of the invention and not to limit the scope of the invention, or its protection, in any manner.

What is claimed is:

1. A medical device loading system, comprising:
a loading apparatus comprising a main body having a proximal end defining a proximal opening, a distal end defining a distal opening, and a passageway extending between the proximal and distal openings, the passageway defining a proximal chamber having a first inner diameter, a distal chamber having a second inner diameter, and a transition chamber disposed between the proximal and distal chambers, the second inner diameter being greater than the first inner diameter and the transition chamber having an inner diameter that transitions along an axial length of the transition chamber from the second inner diameter to the first inner diameter;

a delivery catheter comprising an outer tubular member defining a sheath lumen, a dilator body disposed within the sheath lumen and defining a dilator lumen, and a distal tip member comprising an elongate cannula and a distal tip body, the elongate cannula adapted to be slideably disposed within the dilator lumen and the distal tip body defining an outer diameter that is smaller than the second inner diameter and larger than the first inner diameter; and an expandable intraluminal medical device;

wherein the distal tip member has a separable connection that divides the distal tip member into a proximal distal tip member portion and a distal distal tip member portion when disrupted.

2. The medical device loading system of claim 1, wherein the separable connection is located on the distal tip body such that the proximal distal tip member portion includes a portion of the distal tip body and the distal distal tip member portion includes a portion of the distal tip body.

3. The medical device loading system of claim 1, wherein the distal tip body has a tapered proximal surface.

4. The medical device loading system of claim 3, wherein the separable connection is located proximal to a portion of the distal tip body defining the maximum outer diameter of the distal tip body.

5. The medical device loading system of claim 4, wherein the separable connection is located on the tapered proximal surface of the distal tip body.

6. The medical device loading system of claim 4, wherein the separable connection is located on the tapered proximal surface of the distal tip body such that entire proximal distal tip member portion can be passed through the passageway of the loading apparatus.

7. The medical device loading system of claim 1, wherein the separable connection comprises a connection formed between mating threads.

8. The medical device loading system of claim 1, wherein the main body of the loading apparatus defines a continuous outer surface.

9. The medical device loading system of claim 1, further comprising a proximal cap disposed on the proximal end of the main body, the proximal cap defining a cap passageway in communication with the passageway of the main body; and at least one pull wire attached to the proximal cap and extending into the passageway of the main body.

10. The medical device loading system of claim 9, wherein the at least one pull wire comprises a member selected from the group consisting of a thread, a string, and a suture.

11. The medical device loading system of claim 10, wherein the at least one pull wire comprises two or more pull wires.

12. The medical device loading system of claim 9, further comprising a distal cap disposed on the distal end of the main body.

13. The medical device loading system of claim 12, wherein the distal cap seals the distal opening of the main body.

14. The medical device loading system of claim 13, wherein the proximal cap seals the proximal opening of the main body.

15. The medical device loading system of claim 14, further comprising a storage fluid disposed within the passageway of the main body.

16. The medical device loading system of claim 15, wherein the expandable intraluminal medical device is disposed within the passageway of the main body.

17. The medical device loading system of claim 16, wherein the expandable intraluminal medical device has a radially-expanded configuration and a radially-compressed configuration; and wherein the expandable intraluminal medical device is disposed within the distal chamber of the passageway of the main body in the radially-expanded configuration.

18. A medical device loading system, comprising:

a loading apparatus comprising a main body having a proximal end defining a proximal opening, a distal end defining a distal opening, and a passageway extending between the proximal and distal openings, the passageway defining a proximal chamber having a first inner diameter, a distal chamber having a second inner diameter, and a transition chamber disposed between the proximal and distal chambers, the second inner diameter being greater than the first inner diameter and the transition chamber having an inner diameter that transitions along an axial length of the transition chamber from the second inner diameter to the first inner diameter;

a delivery catheter comprising an outer tubular member defining a sheath lumen, a dilator body disposed within the sheath lumen and defining a dilator lumen, and a distal tip member comprising an elongate cannula and a distal tip body, the elongate cannula adapted to be slideably disposed within the dilator lumen and the distal tip body defining an outer diameter that is smaller than the second inner diameter and larger than the first inner diameter;

an expandable intraluminal medical device including a biologic component;

a proximal cap disposed on the proximal end of the main body, the proximal cap defining a cap passageway in communication with the passageway of the main body; and at least one pull wire attached to the proximal cap and extending into the passageway of the main body;

wherein the distal tip member has a separable connection that divides the distal tip member into a proximal distal tip member portion and a distal distal tip member portion when disrupted.

19. A medical device loading system, comprising:

a loading apparatus comprising a main body having a proximal end defining a proximal opening, a distal end defining a distal opening, and a passageway extending between the proximal and distal openings, the passageway defining a proximal chamber having a first inner diameter, a distal chamber having a second inner diameter, and a transition chamber disposed between the proximal and distal chambers, the second inner diameter being greater than the first inner diameter and the transition chamber having an inner diameter that transitions along an axial length of the transition chamber from the second inner diameter to the first inner diameter;

a delivery catheter comprising an outer tubular member defining a sheath lumen, a dilator body disposed within the sheath lumen and defining a dilator lumen, and a distal tip member comprising an elongate cannula and a distal tip body, the elongate cannula adapted to be slideably disposed within the dilator lumen and the distal tip body defining an outer diameter that is smaller than the second inner diameter and larger than the first inner diameter;

an expandable intraluminal medical device disposed within the passageway of the main body, the expandable intraluminal medical device including a biologic component;

a proximal cap disposed on the proximal end of the main body and sealing the proximal opening;

a distal cap disposed on the distal end of the main body and sealing the distal opening;

wherein the distal tip body defines a tapered proximal surface and the distal tip member has a separable connection on the tapered proximal surface that divides the distal tip member into a proximal distal tip member portion and a distal distal tip member portion when disrupted.

* * * * *